(12) United States Patent
Glocker et al.

(10) Patent No.: US 8,218,724 B2
(45) Date of Patent: Jul. 10, 2012

(54) X-RAY DEVICE

(75) Inventors: Joachim Glocker, Weingarten (DE); Dirk Peters, Baienfurt (DE)

(73) Assignee: Arzneimittel GmbH Apotheker Vetter & Co., Ravensburg (DE)

( * ) Notice: Subject to any disclaimer, the term of this patent is extended or adjusted under 35 U.S.C. 154(b) by 185 days.

(21) Appl. No.: 12/675,074

(22) PCT Filed: Aug. 22, 2008

(86) PCT No.: PCT/EP2008/006902
§ 371 (c)(1),
(2), (4) Date: Feb. 24, 2010

(87) PCT Pub. No.: WO2009/030379
PCT Pub. Date: Mar. 12, 2009

(65) Prior Publication Data
US 2011/0064194 A1    Mar. 17, 2011

(30) Foreign Application Priority Data
Aug. 28, 2007   (DE) .......................... 10 2007 040 488

(51) Int. Cl.
*G01N 23/04* (2006.01)
(52) U.S. Cl. .......................................... 378/57; 378/208
(58) Field of Classification Search ............... 378/57, 378/51, 55, 58, 62, 208, 209
See application file for complete search history.

(56) References Cited

U.S. PATENT DOCUMENTS

| | | | |
|---|---|---|---|
| 5,348,543 A * | 9/1994 | Talley | 604/192 |
| 5,396,889 A * | 3/1995 | Ueda et al. | 600/407 |
| 5,500,886 A | 3/1996 | Duff | |
| 5,590,170 A | 12/1996 | Zweig | |
| 5,909,478 A | 6/1999 | Polichar et al. | |
| 6,229,314 B1 | 5/2001 | Vetter et al. | |
| 6,473,489 B2 * | 10/2002 | Bani-Hashemi et al. | 378/63 |
| 6,776,526 B2 | 8/2004 | Zeiss | |
| 7,522,700 B2 | 4/2009 | Bavendiek et al. | |
| 2002/0191738 A1 * | 12/2002 | Mazess et al. | 378/57 |
| 2003/0002630 A1 * | 1/2003 | Doenges | 378/203 |
| 2004/0028177 A1 | 2/2004 | Pipino | |

(Continued)

FOREIGN PATENT DOCUMENTS

DE          19806971         6/1999

(Continued)

OTHER PUBLICATIONS

English translation of the IPRP, issued Mar. 24, 2010, which includes the English translation of the Written Opinion of the ISA, mailed Nov. 20, 2008.

(Continued)

*Primary Examiner* — Hoon Song
(74) *Attorney, Agent, or Firm* — Harness Dickey & Pierce (57) ABSTRACT

The object of the invention is therefore to provide an x-ray device that is simple to construct and can be inexpensively produced. This object is achieved by the proposed x-ray device for examining syringe caps having a cannula and having the features that is an x-ray source, an x-ray detector, and a holder. The x-ray device is characterized in that the syringe cap is arranged in the beam path so that its longitudinal axis coincides with the main axis of the beam path. The syringe cap is thus impinged from above and from below with x-rays, in order to examine the position of the cannula.

23 Claims, 4 Drawing Sheets

U.S. PATENT DOCUMENTS

2004/0168293 A1  9/2004  Shimazaki
2006/0245542 A1  11/2006  Bavendiek et al.
2007/0147583 A1  6/2007  Wang et al.

FOREIGN PATENT DOCUMENTS

| | | |
|---|---|---|
| DE | 102005020149 | 11/2006 |
| JP | 2001-289753 | 10/2001 |
| JP | 2005-321331 | 11/2005 |

OTHER PUBLICATIONS

"Looking Inside the Box", 3DX-Ray Railway station article, extracted from an article published in Quality Today, Sep. 2003.

* cited by examiner

X-RAY DEVICE

CROSS-REFERENCE TO RELATED APPLICATIONS

This application is a 371 U.S. National Stage of International Application No. PCT/EP2008/006902, filed Aug. 22, 2008. This application claims the benefit of German Patent Application No. DE 10 2007 040 488.5, filed Aug. 28, 2007, the disclosures of which are incorporated herein by reference.

The invention relates to an x-ray system for examining a syringe cap having a cannula in accordance with the superordinate concept of claim 1.

X-ray systems of the type described here are well known. They are used when inspecting syringe caps that contain a cannula. This type of cap is placed on syringes with a cannula on the one hand in order to provide the syringe with the cannula with a sterile cover, and on the other hand as a protection against injuries. Syringe caps of this type frequently include an elastic stopper into which the cannula penetrates. A syringe cap of the type described can be placed on a syringe that has already been provided with a cannula. It can bend when being mounted on the syringe body or can be obliquely inserted thereon and then already be oblique when inserted into the stopper. But a syringe cap of this type can also be provided with a cannula, pre-mounted as-it-were, and then placed on a syringe. Also when being pre-assembled the cannula can be obliquely inserted into the stopper or bent when being inserted. X-ray systems of the type described here are used to detect cannulas that are positioned obliquely in the syringe cap. They have two x-ray sources that can penetrate the syringe cap from two directions, preferably from two directions positioned at 45° to 90°. Using the two images produced it can be determined whether the cannula is obliquely situated inside the syringe cap. In order to prevent the tips of the cannulas from possibly perforating the wall of the syringe cap with the consequent loss of sterility on the one hand, and on the other hand would present the risk of injury, the syringe caps are separated starting with a specific angularity. X-ray devices of this type are expensive because on the one hand two radiation sources and on the other hand an image analysis circuit are required for analyzing the images from the two radiation sources.

The object of the invention is therefore to provide an x-ray device that is simple to construct and can be inexpensively produced.

This object is achieved by the proposed x-ray device for examining syringe caps having a cannula and having the features disclosed in claim 1; that is an x-ray source, an x-ray detector, and a holder. The x-ray device is characterized in that the syringe cap is arranged in the beam path so that its longitudinal axis coincides with the main axis of the beam path. The syringe cap is thus impinged from above and from below with x-rays, in order to examine the position of the cannula. If, with such an arrangement of the syringe cap in the beam path by the x-ray detector at the position, a point is detected at which the cannula is expected, then the cannula is oriented concentrically or coaxially to the beam path. It is thus situated also coaxial to the longitudinal axis of the syringe cap. It is unimportant to this type of examination whether the cannula is housed in a separate syringe cap and placed together with same on the syringe, or whether the syringe cap is placed on a syringe that comprises the cannula. If, however, the cannula is represented as a line in the x-ray detector, then it must be assumed that the cannula does not lie exactly in the longitudinal axis, but at an angle to it. In this instance the cannula is separated.

In a preferred exemplary embodiment of the x-ray device at least one collimator is arranged in the beam path between the x-ray beam source and the examination point. This serves to reduce to a minimum the stress of the beams on the area situated around the examination point.

A particularly preferred exemplary embodiment of the x-ray device is characterized in that additionally a first reference element is provided. This serves to provide a first reference signal when producing an image of the syringe cap in the x-ray detector. The reference element preferably has a circular opening.

Particularly preferred is an exemplary embodiment of the x-ray device that is characterized by a second reference element that is preferably annular in its configuration. This, too, serves to produce a reference signal in the x-ray detector. In virtue of the two reference signals it is particularly easy to decide, whether the cannula runs obliquely; that is at an angle to the longitudinal axis of the syringe cap, and whether the angularity is still acceptable.

Other embodiments of the x-ray device can be read from the subordinate claims.

The invention will be more completely explained in the following using the drawing. Wherein.

Figure 1:
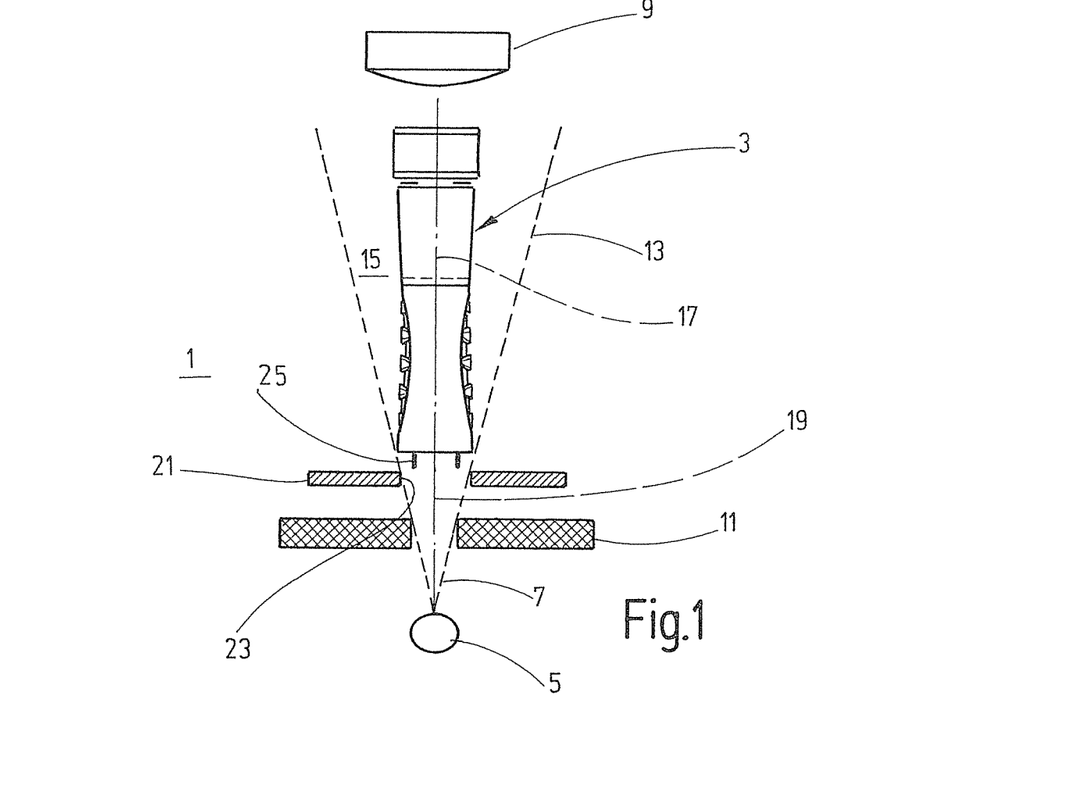
FIG. 1 represents a principle diagram of the x-ray device.

The basic diagram according to FIG. 1 shows an x-ray device 1 that is used for examining a syringe cap 3 as well as an implied x-ray beam source 5, that emits x-ray beams 7. An x-ray detector 9 is provided at a distance from the x-ray beam source 5 which evaluates the x-ray beams impinging thereon. The x-ray beams 7 run a course towards the x-ray detector 9 through a collimator 11, which shields against the radiation exiting from the x-ray beam source 5 and allows only a portion of the x-rays 7 to pass unobstructed toward the x-ray detector 9. There is thus an extended beam path 13 toward the x-ray detector 9. A syringe cap 3 is arranged in same at an examination site 15 in such a fashion that its longitudinal axis 17 coincides with the main axis 19 of the beam path 13. In virtue of this arrangement of the syringe cap 3 on the examination site 15 it is possible to impinge it vertically from above or below with x-ray beams and so to obtain an x-ray image in the x-ray detector 9.

A first reference element 21 is provided on the side of the collimator 11 facing away from the x-ray radiation source, which like the collimator 11, limits the width of the cone of the x-ray beams 7 that run from the x-ray source 5 towards the examination site 15, in order to produce a defined conical beam path 13. The first reference element 21 preferably has a circular opening 23 that is picked up by the x-ray detector and delimits the image represented there. The reference element 21 can be configured ring- or plate-shaped, the circular opening 23 is fundamental.

In FIG. 1, a second reference element 25 is arranged between the x-ray source 5 and the x-ray detector 9—here above the first reference element 21—which, like the collimator 11 and the first reference element 21, is arranged in the region of the x-ray beams 7 emitted by the x-ray source 5. Seen from the x-ray source 5, the second reference element 25 is situated downstream of the beam relative to the first reference element. In the preferred exemplary embodiment represented here, it is arranged directly before the examination site 15. In another preferred exemplary embodiment (not shown here) the second reference element 15 is arranged in the beam path opposite the examination site 15, preferably directly in front of the x-ray detector 9. The second reference element 25 is configured annular and thin-walled and is represented as a thin ring in the x-ray detector 9.

The external diameter of the second reference element 25 is smaller than the inside diameter of the opening 23. It is arranged concentric to the main axis 19 of the beam path 13. This applies also to the opening 23 of the first reference element 21.

Figure 2A:
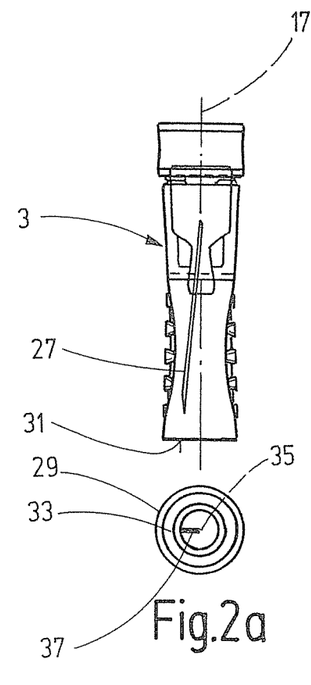
FIG. 2 represents three syringe caps and their images taken at the time of x-ray examination.
Figure 2B:
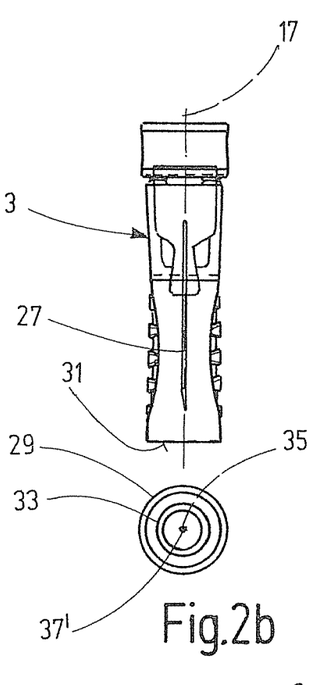
Figure 2C:
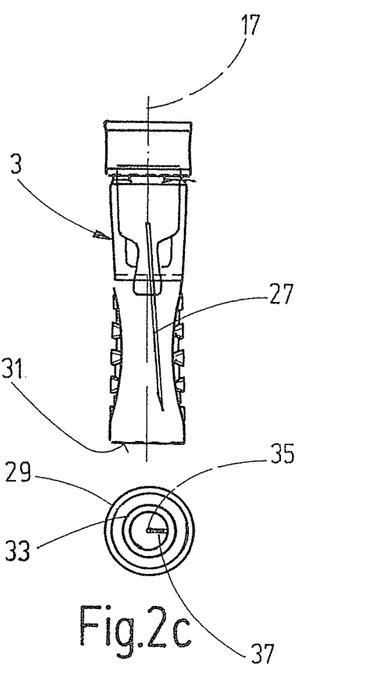

FIG. 2 shows three syringe caps 3 as are represented also in FIG. 1. Here in FIG. 2 the cannula 27 that is situated on the inside of the syringe cap 3 is seen. In the left representation in FIG. 2 the cannula 27 is not arranged concentric to the longitudinal axis 17 of the syringe cap 3. Rather, it runs opposite same to the left so that it includes an acute angle opening downwards having the longitudinal axis 17 (FIG. 2). The deflection of the cannula 27 can naturally lie also in a plane other than the image plane of FIG. 2.

Underneath the left tip cap an image a) is reproduced as it is detected by the x-ray detector 9 shown in FIG. 1. The wall of the syringe cap 3 transilluminated from the upper side is represented as an external ring 29. Concentric to the outside ring 29 a thin inside ring 33 can be seen, which represents the image of the second reference element 25.

A black line runs to the left from the center point 35 of the inside ring 33 and represents the image 37 of the cannula 27 deflected to the left.

In the center representation in FIG. 2 the cannula 27 runs concentrically to the longitudinal axis 17 of the syringe cap 3. In the illustration b) shown thereunder the syringe cap 3 can be seen that the cannula 27 in the x-ray detector 9 is represented in this case as a point 37' that coincides with the center point 35 of the inside ring 33, through which the longitudinal axis 17 of the syringe cap 3 also runs.

The syringe cap 3 with a cannula 27 deflected to the right can be seen at the upper right in FIG. 2. Thereunder the illustration c) of a syringe cap 3 of this type is shown in the x-ray detector 9: It can be seen that here a line running to the right between the center point 25 and the inside ring represents the depiction 37 of the cannula 27.

Finally, it is clear that a correctly concentrically depicted cannula 27 is depicted as point 37' that coincides with the center point 35 of the inside ring 33. As soon as the cannula 27 of the longitudinal axis 17 of the syringe cap 3 is deflected—that is, bent—it is depicted as a line.

A still acceptable measure of deflection of the cannula 27 can be defined in virtue of the inside diameter of the inside ring 33. If this is maximally bent vis-à-vis the longitudinal axis 17 of the syringe cap 3 that it contacts the inside ring 33, the syringe cap 3 is classified as conforming. If, however, the depiction 37 of a deflected cannula 27 ends outside of the inside ring 33, the associated syringe cap 3 would be segregated as unacceptable.

The three illustrations a), b), and c) in FIG. 2 of the syringe cap 3 depicted in this illustration show that it is possible in simple fashion to differentiate syringe caps 3 with concentric cannula 27 from those, in which the cannula is bent or deflected vis-a-vis the longitudinal axis 17 of the syringe cap 3. Here it makes no difference whether the cannula 27 is mounted obliquely in a syringe on which the syringe cap 3 is placed, or whether the cannula 27 is deflected from its originally correct position when placing the syringe cap 3.

The x-ray device 1 is can thus be used for examining syringe caps 3 that are pre-assembled and already comprise a cannula 27. They can also be used for examining syringes having a cannula fixed on the syringe body and on which a syringe cap has been placed. When this is done, it is possible in both cases to x-ray the syringe cap 3 from its top side 31 or from the opposite side. It is critical only that the syringe cap 3, and with it also an associated syringe, if applicable, is arranged on the examination site 15 concentrically to the main axis 19 of the cone-shaped beam path 13, so that the longitudinal axis 17 of the syringe cap 3 coincides with the main axis 19.

Figure 3:
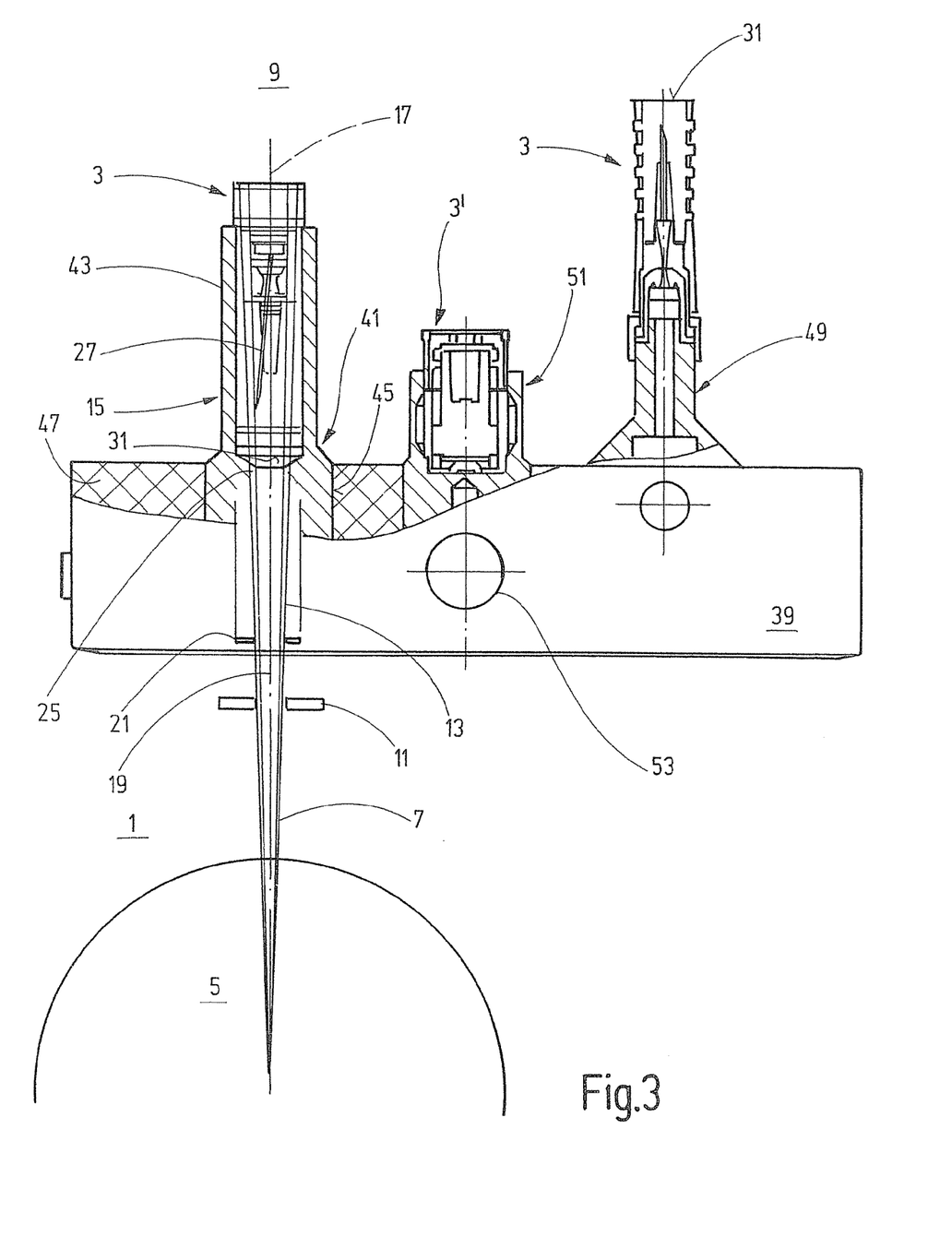
FIG. 3 represents a first exemplary embodiment of an x-ray device.

A first exemplary embodiment of an x-ray device 1 is shown in FIG. 3 which operates according to the basic principle described using FIGS. 1 and 2 and used for examining a syringe cap 3 having a cannula 27, in order to establish whether the cannula 27 is or is not deflected vis-à-vis the longitudinal axis 17 of the syringe cap 3.

The x-ray source 5 of the x-ray device can be seen in FIG. 3; in addition the collimator 11, the first reference element 21, and the second reference element 25. Also shown are the x-ray beams leaving the x-ray source 5, which pass through the collimator 11 and the first reference element 21, and produce a conical beam path 13.

In this exemplary embodiment, on the side of the first reference element 21 facing away from the x-ray source 5 the second reference element 25 is situated directly in front of the syringe cap 3 arranged at the examination site 15. It is likewise configured ring-shaped, as shown in FIG. 1.

The x-ray detector 9 (not shown here) that delivers the image of the syringe cap is situated over the syringe cap 3.

In the exemplary embodiment of the x-ray device 1 shown in FIG. 3, a mounting device 29 installed in the beam path 13 is provided, which comprises a first receiving unit 41. This holds the syringe cap 3 in the desired orientation at the examination site 15. It has a cylindrical section 43 whose inside diameter is selected so that it receives the syringe cap 3 in its inside as snugly as possible and whose middle axis coincides with the main axis 19 of the beam path 13. When this is done, the syringe cap 3 is so arranged vis-à-vis the beam path 13 that its longitudinal axis 17 coincides with the main axis 19 of the beam path 13. Here the syringe cap 3 is x-rayed from its upper side 31. It is also conceivable that the first receiving unit 41 is embodied so that the syringe cap 3, with an associated syringe, if necessary, is conversely held on the examination site 15 and thus is x-rayed from below.

The first receiving unit 41 is embodied as an insert. It can thus be plugged into an appropriate recess 45 in the base 47 of the retaining device 39. In this fashion it is also possible to combine different first receiving units 41 using one and the same retaining device 39.

FIG. 3 shows that the retaining device 39 comprises a second receiving unit 49, on which the syringe cap 3 can be slipped. In the exemplary embodiment of the retaining device 39 represented here, the second receiving unit 39 is so embodied that with such a mounting the syringe cap 3 can be held with its upper side 31 facing upwards by the second receiving unit 49. It is clear that the syringe cap 3 must be rotated 180° before installation in the cylindrical section 43 of the first receiving unit 42. This can be done manually or using appropriate manipulators.

The second receiving unit 49, too, can be embodied as an insert that can be inserted into the retaining device—and thus interchangeably—in order to be able to adapt the mounting 39 to the different syringe caps 3.

In the exemplary embodiment shown in FIG. 3 the retaining device 39 has a third receiving unit 51 that is embodied differently than the other receiving units. It can be used to receive another type of syringe cap 3' or the like, that is to be examined using the x-ray device 1 and held at the examination site 15, when the x-ray examination is to be done.

Preferred is an exemplary embodiment of the retaining device 39 that has several identical receiving units that are embodied like the first receiving unit 41. This type of receiving units could be arranged circularly in the base 47 of the retaining device 39, for example. It is then possible to rotate the retaining device 39 after examining a first syringe cap 3, until the next receiving unit is arranged with a syringe cap 3 at the examination site 15. The receiving units can also be arranged in a row in the base 47 of the retaining device 39. In this instance, the retaining device 39 is then subject to a transverse movement, in order to bring the receiving units with the syringe caps sequentially to the examination site 15 and examine them.

The retaining device 39 is preferably provided with a data storage medium 53, which is merely implied here. When examining syringe caps 3 it is also possible to supply them in batches by means of a retention device 39 for examination using an x-ray device 1. The retaining device 39 can then be detected and stored for tracking a manufacturing process.

In FIG. 3 it can be seen that the collimator 11 is arranged under the retaining device 39 and that the first reference element 21 is situated somewhat above the underside of the retaining device 39. It is quite possible to bring the first reference element 21 closer to the examination site 15 and to the position of the second reference element 25 represented in FIG. 3, for example. The results in the beam of the x-ray source 5 being even better focused on the examination site 15. In this case the second reference element 25 is then—viewed in the direction of irradiation—placed on the side of the examination site facing away from the x-ray source 5, in front of the x-ray detector 9. Preferably it can be arranged immediately in front of the x-ray detector 9 so that a particularly sharp image of the second reference element 25 results and so that it can also be displayed as a very thin ring.

Ultimately two annular reference elements of the type discussed here or in the following and that are concentric to each other can be used. A tolerance range can thus be defined, within which a deflection of the cannula 27 can still be accepted.

Figure 4:
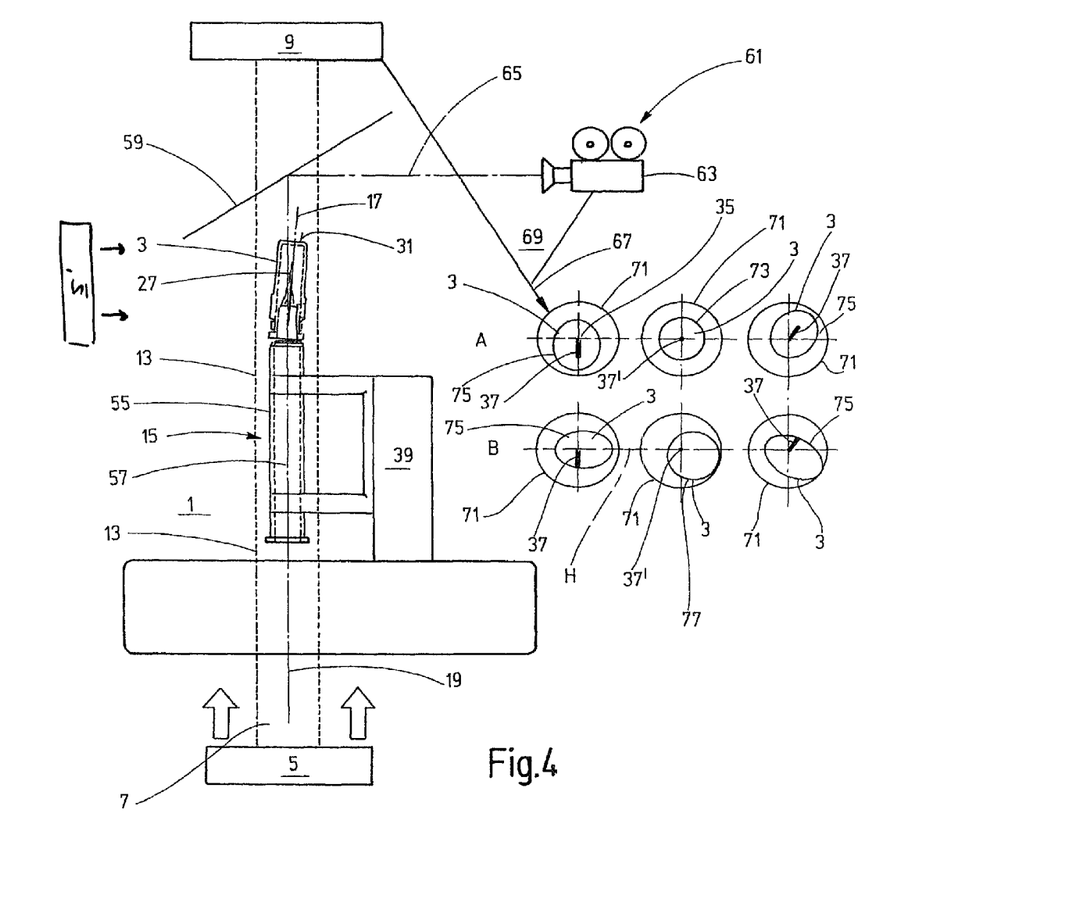
FIG. 4 represents a second exemplary embodiment of an x-ray device.

A transformed exemplary embodiment of the x-ray device 1 is shown in FIG. 4. Identical and functionally analogous parts are provided with the same reference numbers. Inasmuch, reference is made here to the previous description.

The x-ray device 1 has an x-ray beam source 5, which emits x-ray beams 7 towards an x-ray detector 9. A beam path 13 is merely implied here. Its main axis 19 runs here in FIG. 4 vertically upward from the x-ray source 5 through the examination site 15 to the x-ray detector 9.

Here a syringe 55 can be seen on the examination site 15 where it is held by a suitable retaining device 29 on the examination site 15 and so aligned that its longitudinal axis 57 coincides with the main axis 19 of the beam path 13.

A syringe cap 3 is placed on the syringe 55 and said cap is seated here obliquely on the syringe 55 such that the longitudinal axis 17 of the syringe cap 3 exhibits an angle to the main axis 19 of the beam path 13.

It can be clearly seen that in the exemplary embodiment according to FIG. 4 the syringe 55 and the syringe cap 3 are transradiated from below. The syringe cap 3 is thus so arranged—differently than in the case of the representations according to FIGS. 1 to 3—that its top side 31 faces upwards. At least one additional x-ray source 5' may be provided which transradiates the examination site 15 from one side.

A deflection device 59, permeable to x-rays but deflecting light rays, and having a mirror, is arranged in the beam path 13A and—viewed from the x-ray source 5—on the other side of the examination site 15.

The x-ray device 1 has an image detection unit 61 that comprises a camera 63, for example. A broken line 65 is used to indicate that the image detection unit detects an image from the top side 31 of the syringe cap 3.

The x-ray detector 9 signals and those of the image detection unit 61 are pooled and, as indicated by a line 67, evaluated together; that is, superimposed. An image analysis unit 69 is used for analyzing the x-ray detector 9 signals and the image detection unit 61 signals, which are not individually represented here.

A indicates the overlapping of the image signals of the x-ray detector 9 and the image detection unit 61: A target position lying concentrically to the main axis 19 is specified using an external circle 71, said position corresponding to the syringe 55, for example.

In the middle a concentric inner circle 73 can be seen in the case of A. This indicates the optical image of a syringe cap 3 with a concentric arrangement; that is, when its longitudinal axis 17 coincides with the main axis 19 of the beam path 13. In this instance, the cannula 27 is depicted as a point 37' when it is arranged coaxial to the longitudinal axis of the syringe cap 3.

In the depictions according to A the external circle 71 can be seen to the left. Inside the circle 71, the depiction can be seen of a syringe cap 3 arranged oblique to the main axis 19 of the beam path 13, which is seen as an ellipse 75 by the image detection unit 61. It can also be seen that a line is visible extending from the center point 35 of the external circle 71, said line representing the image 37 detected by the x-ray detector 9 of a correspondingly deflected cannula 27.

It is clear that the cannula 37 is deflected in the same direction as the syringe cap 3. It is thus assumed that the syringe cap 3 and the cannula 27 are bent in the same direction, that the cannula 27 does not anywhere penetrate the external wall of the syringe cap 3, and that accordingly this syringe cap 3 is acceptable.

Accordingly to the far right in the illustrations according to A, an external circle 71 can be seen. Here, too, the image detection unit 61 recognizes that the syringe cap 3 is deflected upwards to the right. Here, too, this can be seen in virtue of the ellipse 75. The depiction 37 of the cannula 27 lies on the central axis of the ellipse 75. It is therefore assumed that the syringe cap 3 and the cannula 27 are deflected in the same direction, and thus the cannula 27, as in the left illustration according to A, is arranged concentrically to the syringe cap 3. The illustrations labeled with A thus show syringe caps 3 that all conform.

If one considers the illustration B in FIG. 4, which results by an overlapping of the images of the x-ray detector 3 and the image detection unit 61, then here too the external contour of the syringe 55, which is detected by the x-ray detector 9, can be seen and is indicated by an external circle 71. In the case of the left illustration according to B the image detection unit 61 recognizes that the syringe cap 3 is deflected to the right and the central axis of the ellipse lies on a conceptualized horizontal H. The x-ray detector 3 shows the depiction 37 of the cannula 27 as a line. It is obviously deflected vertically downwards; that is, not in the direction of the central axis of the ellipse 75. The image analysis unit 69 thus recognizes that the syringe cap 3 does not conform.

A corresponding deviation of the central axis of the ellipse 75 and the resulting deflection of the syringe cap 3 from the deflection of the cannula 27, which is depicted by the x-ray detector 9 by the line 37, is shown also in the far right of illustration B. This syringe cap 3, too, is recognized by the image analysis unit 69 as being defective.

In the center of the illustration according to B the following can be seen: Again a target position or the wall of the syringe 55 recognized by the x-ray detector 9 is in turn specified. A point 37' coinciding with the center point of the circle 71 shows the cannula 27 aligned concentrically to the main axis 19 of the beam path 13. The image analysis unit 69 has recognized that the syringe cap 3 is seated obliquely, which is indicated by a circle 77 depicted eccentrically to the center point of the circle 77. It is clear that the longitudinal axis 17 of the syringe cap 3 does not coincide with the cannula 27. The analysis of the x-ray image by means of the x-ray detector 9 and the detection of the syringe cap 3 by the image detection unit 61 thus indicate that here there is an incorrect alignment of the cannula 27 inside the syringe cap 3. Here, too, the image analysis unit 6 recognizes a defective product so that it can be segregated.

Figure 5:
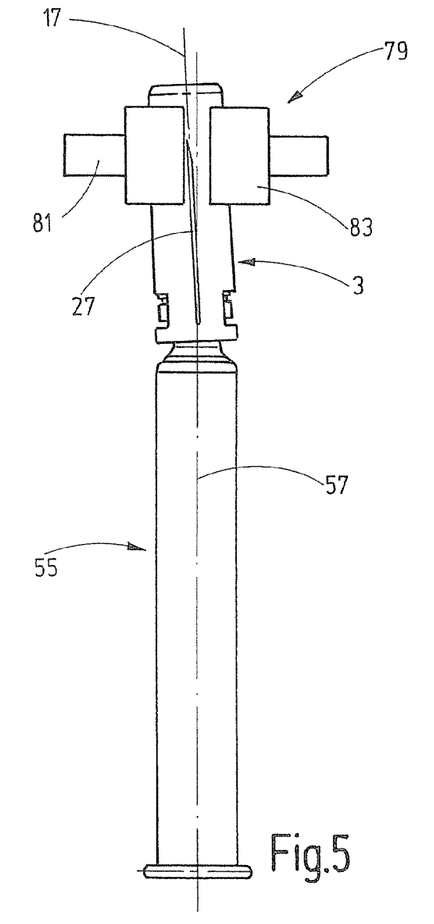
FIG. 5 represents a side view of a syringe with an obliquely seated syringe cap.

FIG. 5 represents a side view of a syringe 55 with a syringe cap 3. Parts that have already been explained using the previous Figures are provided with the same reference numbers.

The syringe 55 has a longitudinal axis 57, opposite which the longitudinal axis 17 of the syringe cap is pivoted. In FIG. 5 the syringe cape 3 is tipped at an acute angle to the left because it is not correctly applied to the syringe 55. Therefore the needle 27 (only indicated in FIG. 5) situated in the syringe cap is also tipped vis-à-vis the central axis 57 of the syringe 55.

FIG. 5 shows an alignment device 79. This serves to correctly align the syringe cap 3 vis-à-vis the syringe 55 so that alignment errors are prevented. With the aid of the alignment device 79 the syringe cap 3 is aligned so that its longitudinal axis 17 aligns with the central axis 57 of the syringe 55.

The alignment device 79 is embodied so that it embraces the syringe cap 3. Here it has two gripper elements 81 and 83 arranged at a distance from each other. There separation is selected so that the syringe 55 even with a crookedly seated syringe cap 3 can be arranged between the gripper elements 81, 83.

Figure 6:
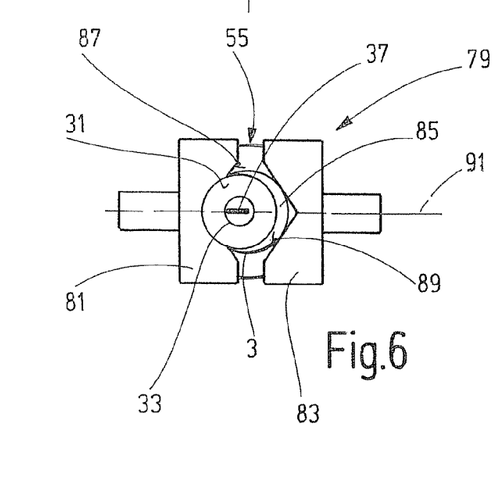
FIG. 6 represents a top view of the syringe with the syringe cap according to FIG. 5.

FIG. 6 shows the syringe 55 according to FIG. 5 viewed from the top. The syringe cap 3 can be identified. Here not only its top side 31 but also parts of its peripheral surface 85 can be seen. Optical image detection can thus easily recognize the incorrect seating of the syringe cap 3.

If the syringe 55 illustrated here with the obliquely seated syringe cap 3 is imaged from top to bottom or from below upwards using the x-ray device 1 as described above, the cannula 27 will be represented as a line. The depiction 37 of the cannula 27 is drawn in FIG. 6.

The x-ray device 1 is embodied so that the oblique seating of the cannula 27 can be identified using the line depiction 37 of the cannula 27. It is also conceivable to use the depiction of the syringe cap 3 represented by the image detection unit 61 for identifying its oblique seating. Preferably, the signals of the x-ray detector 9 and of the image detection unit 61 will be analyzed together, particularly overlapped.

The depiction 37 of the cannula 27 proceeds from the central axis 57 of the syringe 55 and runs from there essentially horizontally to the left. Accordingly a crescent-shaped region of the peripheral surface 85 can be identified to the right of the circularly depicted top side 31 of the syringe cannula 3. Using the depiction 37 of the cannula 27 detected by means of the x-ray detector 9 and using the position of the peripheral surface 85, which is depicted crescent-shaped in FIG. 6, the direction in which the syringe cap 3 and the cannula are pivoted can be established.

The alignment device 79 can now specifically effect a counter-movement of the syringe cap 3.

Preferably the gripper elements 81 and 83 of the alignment device 79 have V-shaped inside surfaces 87 and 89, whereby the intersection points of the surface segments of the inside surfaces 87 and 89 lie on a conceptual line 91 which runs through the central axis 57 of the syringe 55.

Figure 7:
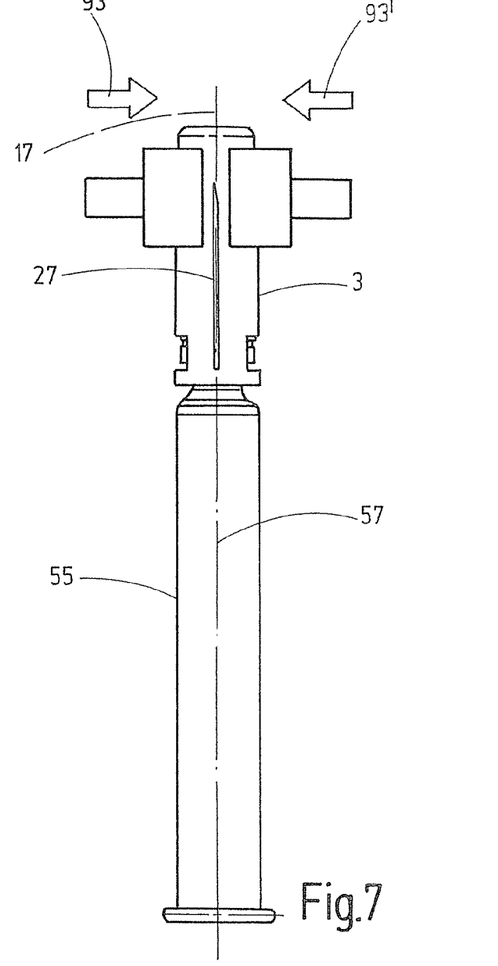
FIG. 7 represents a side view of a syringe with a correctly seated syringe cap.

FIG. 7 again represents the syringe 55 illustrated in FIG. 5 in side view. Arrows 93, 93' indicate that the gripper elements 81 and 82 are moved towards each other; that is, in the direction towards the central axis 57 of the syringe 55. These act on the syringe cap 3 so that its longitudinal axis 17 aligned with the central axis 57, so that they are arranged correctly on the syringe 55. Accordingly the cannula 27, too, lies coaxial to the longitudinal axis 17 and thus to the central axis 55.

Figure 8:
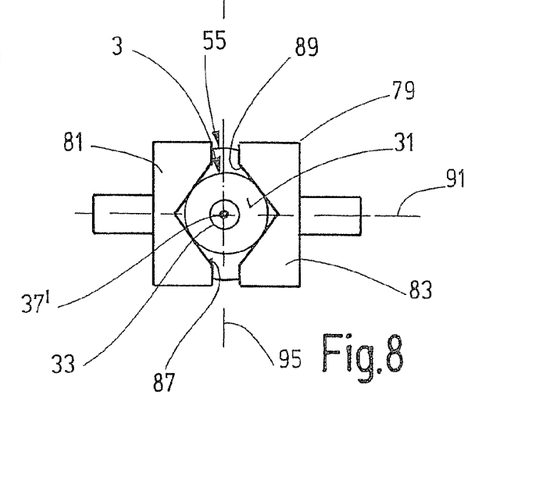
FIG. 8 represents a top view of the syringe with the syringe cap according to FIG. 7.

It can be seen in the top view according to FIG. 8 that the inside surfaces 87 and 89 in this position center the syringe cap 3 so that the cannula 27 is depicted as a point 37' by the x-ray device 1 or its x-ray detector 9. Optical detection of the syringe cap 3 would depict its top side 31 as a circle. Any regions of the peripheral surface 85 of the syringe cap 3 are no longer visible here. The depiction of the cannula obtained by the x-ray detector 9 and the image of the syringe cap 3 generated by an image detection unit 61 show that the cap is not correctly aligned.

The syringe cap 3 is aligned exactly vis-à-vis the central axis 57 of the syringe 55 by the gripper elements 81, 83 moved toward each other and by their V-shaped inside surfaces 87 and 89. The adjustment vis-à-vis the conceptual line 91 is made in that the V-shaped inside surfaces 87 and 89 are oriented to this line. If the gripper elements 81 and 83 are moved symmetrically to a conceptual central plane 95, which runs through the central axis 57 of the syringe 55 and stands vertical to the line 91, an exact alignment of the syringe cap 3 vis-à-vis this central axis 95 is possible without further ado. Activation of the alignment device can be done automatically if the x-ray detector 9 and/or the image detection unit 61 indicate(s) an incorrect position of the syringe cap vis-à-vis the syringe 55.

It should be reiterated that the embodiment of the alignment device 79 can also be altered. It is conceivable, for example, to align the syringe cap 3 by means of one or a plurality of optionally shaped grippers using the analysis of the image obtained from the x-ray detector 9 or the image detection unit 61 that the surface 31 is aligned concentrically to the central axis 57 of the syringe 55 or the cannula 27 is depicted as a point 37'.

If it is not possible to align the top side 31 concentrically to the central axis 57 and simultaneously to depict the cannula 27 as a point on the intersection of the central plane 59 with the line 91, it must be assumed that the cannula 27 is not arranged concentrically relative to the syringe cap 3.

In FIGS. 6 and 8 the inside ring 33 is indicated by a line that is depicted by using a second reference element 25 in the x-ray detector 9. This serves to establish whether or not, if the cannula 27 is deflected out of the desired central position, it still lies in the acceptable region. Inasmuch reference is made to the statements relating to the image analysis according to FIGS. 2 and 4 (see illustrations A and B there).

Overall it can be seen that the imaging of a syringe cap 3 together with a syringe 55, if necessary, using an x-ray device 1 easily enables examination of whether the cannula 27 is correctly arranged inside the syringe cap 3, or lies at least within a tolerance range, which with the aid of a second reference element 25 or of the inside ring 33 can be defined and read.

At all events a single x-ray source 5 is sufficient for imaging the syringe cap 1 from above or from below, while it is arranged coaxially to the beam path 13 of the x-ray source 5, while thus its longitudinal axis 17 coincides with the main axis 19 of the beam path 13.

From the explanations relating to the x-ray device the following becomes obvious: The x-ray device images the syringe cap 3 along its longitudinal axis 17. It can differentiate glass and plastic from metal. In this fashion it is possible to detect a cannula 27 made of metal inside the syringe cap 3 and to do this regardless of whether the cannula is provided as a pre-assembled element of the syringe cap 3 or is mounted on the syringe, on which the syringe cap 3 is placed.

The critical criterion of the x-ray device 1 is the possibility of detecting metal objects in an environment that contains glass and/or plastic.

The x-ray device described using the Figures is characterized in that the syringe cap 3 to be imaged is impinged with beams along its longitudinal axis. In addition it can also be provided that the examination site 16 is impinged also laterally with x-rays, in order to obtain additional information on the alignment of the cannula 27 in the syringe cap 3. When this is done the examination direction and the number of examinations can be freely selected in a wide range, in order to achieve maximum reliability with regard to product quality. As a rule, a syringe or its syringe cap 3 arranged on the examination site will be imaged laterally, from the same height. But it is also possible to arrange the x-ray source so that the syringe cap 3 can be examined laterally obliquely from below or above. The examinations can also be carried out at different angles vertically to the optimum course of the cannula 27 so that in the doubtful case exact information on the course of the cannula 27 inside the syringe cap 3 can be obtained.

Therefore, all devices that examine the syringe cap 3 using beams, in order to detect the course of a cannula 27 inside the syringe cap 3 should be included in the term "x-ray device". Therefore, the invention is thus not particularly limited to x-ray but includes all irradiation types that enable a similar type of examination of the syringe cap 3.

The invention claimed is:

1. An x-ray device for examining syringe caps with a cannula, the x-ray device comprising:
   an x-ray source;
   an x-ray detector;
   a holder holding the syringe cap in a beam path at an examination site, wherein the syringe cap is arranged in the beam path so that a longitudinal axis of the syringe cap coincides with a main axis of the beam path; and
   a first reference element being annular and thin-walled, the first reference element being disposed between the x-ray source and the examination site, such that the first reference element is represented as a thin ring in the x-ray detector.

2. The x-ray device according to claim 1, further comprising at least one collimator arranged in the beam path between the x-ray source and the examination site.

3. The x-ray device according to claim 1, further comprising a second reference element having an opening, the second reference element disposed between the x-ray source and the examination site.

4. The x-ray device according to claim 2, further comprising a second reference element, the second reference element disposed between the at least one collimator and the examination site.

5. The x-ray device according to claim 3, wherein the first reference element is disposed between the second reference element and the examination site.

6. The x-ray device according to claim 1, wherein the first reference element is arranged directly in front of the examination site when viewed in the direction of radiation.

7. The x-ray device according to claim 1, wherein the first reference element is arranged directly in front of the x-ray detector when viewed in the direction of radiation.

8. The x-ray device according to claim 1, wherein the first reference element is a thin ring.

9. The x-ray device according to claim 1, further comprising an image detection unit.

10. The x-ray device according to claim 1, further comprising a deflection device arranged between the examination site and the x-ray detector.

11. The x-ray device according to claim 9, wherein an image of the x-ray detector and an image of the image detection unit is supplied to an image analysis unit.

12. The x-ray device according to claim 11, wherein the images of the x-ray detector and the image detection unit are overlapped.

13. The x-ray device according to claim 1, further comprising an alignment device arranged in a region of the examination site.

14. The x-ray device according to claim 1, further comprising a retaining device with a first receiving unit for the syringe cap positionable into the beam path.

15. The x-ray device according to claim 14, wherein the retention device has at least a second receiving unit.

16. The x-ray device according to claim 14, wherein the retention device has at least a third receiving unit.

17. The x-ray device according to claim 14, wherein at least the first receiving device is an insert insertable into the retention device.

18. The x-ray device according to claim 1, further comprising at least one additional x-ray source for transradiating the examination site from one side.

19. A method for examining a syringe cap having a cannula, wherein the examination is carried out with an x-ray device comprising an x-ray source, an x-ray detector, and a holder for holding the syringe cap, the method comprising:
   holding the syringe cap by the holder in a beam path of the x-ray device between the x-ray source and the x-ray detector so that a longitudinal axis of the syringe cap coincides with a main axis of the beam path;
   recording at least one image of the cannula of the syringe cap with the x-ray detector; and
   comparing a shape and a size of the representation of the cannula within the image with a predetermined still acceptable deviation of the cannula with respect to the longitudinal axis of the syringe cap as defined in a reference image.

20. The method according to claim 19, wherein the reference image is included in the x-ray image of the syringe cap, and comprises a representation of a reference element, and comprising classifying the syringe cap as conforming when a representation of the cannula in the x-ray image at most contacts a boundary defined by the representation of the reference element, and classifying the syringe cap as non-conforming when the representation of the cannula extends beyond the respective boundary.

21. The method according to claim 20, comprising: representing the reference element as a thin ring in the x-ray image, and classifying the syringe cap as conforming if the representation of the cannula at most contacts the ring, and classifying further the syringe cap as non-conforming if the representation of the cannula in the x-ray image ends outside the ring.

22. The method according to claim 19, wherein the reference image is a visible image of the syringe cap recorded by an image detection unit, and wherein the x-ray image recorded by the x-ray detector is superimposed on and compared with the visible image by an image analysis unit.

23. The method according to claim 22, wherein the x-ray image and the visible image are compared in order to decide whether the syringe cap and the cannula are bent at all, deflected in the same direction, or whether the cannula is deflected in a different direction than the syringe cap.

* * * * *